(12) United States Patent
Eger

(10) Patent No.: US 7,850,512 B2
(45) Date of Patent: Dec. 14, 2010

(54) METHOD FOR DETERMINING PHYSIOLOGICAL PARAMETERS OF A SLAUGHTERED ANIMAL BODY

(76) Inventor: Horst Eger, Rebhuhnwinkel 8, 16356 Ahrensfelde (DE)

(*) Notice: Subject to any disclaimer, the term of this patent is extended or adjusted under 35 U.S.C. 154(b) by 699 days.

(21) Appl. No.: 11/663,932

(22) PCT Filed: Sep. 27, 2005

(86) PCT No.: PCT/EP2005/010577

§ 371 (c)(1),
(2), (4) Date: Mar. 27, 2007

(87) PCT Pub. No.: WO2006/034871

PCT Pub. Date: Apr. 6, 2006

(65) Prior Publication Data

US 2007/0275647 A1    Nov. 29, 2007

(30) Foreign Application Priority Data

Sep. 27, 2004    (DE) .................. 10 2004 047 773

(51) Int. Cl.
*A22C 25/00* (2006.01)
(52) U.S. Cl. .................................................. 452/156
(58) Field of Classification Search .................... 452/52, 452/53, 149, 150, 156–159
See application file for complete search history.

(56) References Cited

U.S. PATENT DOCUMENTS

| | | | | |
|---|---|---|---|---|
| 4,745,473 A | * | 5/1988 | Hall | 348/396.1 |
| 4,785,817 A | * | 11/1988 | Stouffer | 600/443 |
| 5,079,951 A | * | 1/1992 | Raymond et al. | 73/602 |
| 5,194,036 A | * | 3/1993 | Chevalier et al. | 452/198 |
| 5,208,747 A | * | 5/1993 | Wilson et al. | 600/443 |
| 5,314,375 A | * | 5/1994 | O'Brien et al. | |
| 5,334,084 A | * | 8/1994 | O'Brien et al. | 452/157 |
| 5,705,749 A | * | 1/1998 | Manns et al. | 73/602 |
| 5,717,142 A | * | 2/1998 | Schafer | 73/597 |
| 5,793,879 A | * | 8/1998 | Benn et al. | 382/110 |
| 5,937,080 A | * | 8/1999 | Vogeley et al. | 382/110 |
| 5,944,598 A | * | 8/1999 | Tong et al. | 452/158 |
| 5,960,105 A | * | 9/1999 | Brethour | 382/141 |
| 6,013,031 A | * | 1/2000 | Mendlein et al. | 600/442 |

(Continued)

FOREIGN PATENT DOCUMENTS

DE    41 09 345 A1    9/1991

(Continued)

*Primary Examiner*—Thomas Price
(74) *Attorney, Agent, or Firm*—Kriegsman & Kriegsman

(57) ABSTRACT

The invention concerns a method for determining physiological parameters of a slaughtered animal body or piece thereof with respect to determining its commercial value and/or its processing. The method will lead to a more exact calculation of meat proportions and weight proportions and preferably to a more precise determination of cutting-up points for automated cutting up, in particular by including volumetric parameters.

Figure 1:
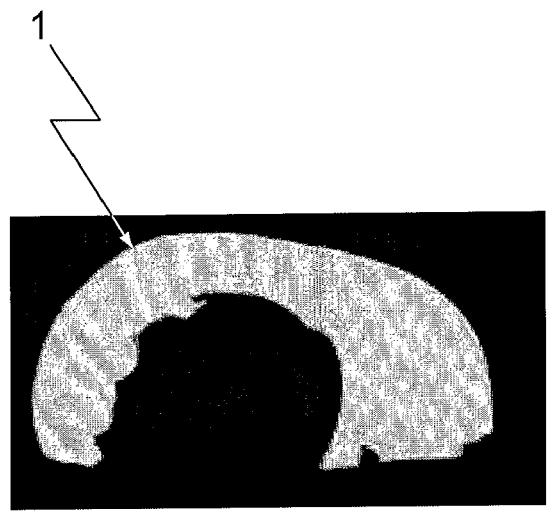

In order to solve the problem, the object, i.e., the slaughtered animal body or one of its pieces, is acquired by means of an image acquisition device. Then a software-supported evaluation of the image acquired from the respective object is made. According to the invention, the object to be evaluated is thus acquired, however, not with a video system of the conventional type, but rather a tomographic method, such as computer tomography or nuclear spin tomography is used as the imaging method.

4 Claims, 1 Drawing Sheet

U.S. PATENT DOCUMENTS

| | | |
|---|---|---|
| 6,028,907 A | 2/2000 | Adler et al. |
| 6,099,473 A * | 8/2000 | Liu et al. ................... 600/449 |
| 6,104,827 A * | 8/2000 | Benn et al. ................. 382/110 |
| 6,167,759 B1 * | 1/2001 | Bond et al. .................. 73/602 |
| 6,170,335 B1 * | 1/2001 | Clinton ....................... 73/629 |
| 6,198,834 B1 | 3/2001 | Belk et al. |
| 6,370,223 B1 * | 4/2002 | Gleason et al. .............. 378/58 |
| 6,609,423 B1 * | 8/2003 | Retterath et al. ............. 73/433 |
| 6,735,326 B1 * | 5/2004 | Schimitzek ................ 382/110 |
| 6,829,927 B2 * | 12/2004 | Retterath et al. ............. 73/149 |
| 6,891,961 B2 * | 5/2005 | Eger et al. ................. 382/110 |
| 6,974,373 B2 * | 12/2005 | Kriesel ...................... 452/157 |
| 7,039,220 B2 * | 5/2006 | Kriesel ...................... 382/110 |
| 7,128,024 B2 * | 10/2006 | Doyle, II |
| 7,214,128 B2 * | 5/2007 | Kriesel ...................... 452/157 |
| 7,265,356 B2 * | 9/2007 | Pelizzari et al. ........ 250/370.09 |
| 7,347,161 B2 * | 3/2008 | Pratt |
| 7,399,220 B2 * | 7/2008 | Kriesel et al. .............. 452/157 |
| 2003/0181156 A1 | 9/2003 | Pascual |

FOREIGN PATENT DOCUMENTS

| | | |
|---|---|---|
| DE | 44 08 604 A1 | 12/1995 |
| DE | 199 52 628 A1 | 5/2001 |
| WO | WO 92/05703 A1 | 4/1992 |

* cited by examiner

METHOD FOR DETERMINING PHYSIOLOGICAL PARAMETERS OF A SLAUGHTERED ANIMAL BODY

The invention concerns a method for determining physiological parameters of a slaughtered animal body, wherein the parameters are determined for the purpose of automatic evaluation with regard to determining commercial value and/or for processing of the slaughtered animal bodies. It relates to the qualitative evaluation of the slaughtered animal body overall, but also, in particular, of individual parts or pieces, at an early time point in its processing. The subject of the invention is also to find points for cutting up the slaughtered animal body in an automated method, which points are to be viewed as optimal for rational processing, the assurance of a high product quality and preserving the economic interest of meat producers.

Industrial meat production has for some time been subject to a high degree of automation that is continually increasing. This derives in part from relieving the persons who work in this field from stringent manual labor, but also, in particular, in order to assure a high quality standard in the interest of the consumer. This is also in accord with the economic requirements of the producing concerns, which are subject to ever increasing price pressure. Taking into consideration this mix of positions, in the past, a number of methods have been developed which make it possible to obtain information on the quality of meat even at an early stage of processing. Thus, methods have become known, by means of which information can be obtained on meat, fat and weight proportions on the still largely intact slaughtered animal body. Corresponding information refers to the slaughtered animal body overall or to parts to be separated out in the course of cutting up, for example, information for determining a ham weight or for dividing tissue compartments in the region of the cutlet or roast. Methods based on ultrasound and/or evaluation and classification by video technology are used for this purpose.

Thus, for example, DE 4,408,604 C2 describes an evaluation method, in which the tissue compartments of meat and fat as well as of meat or fat and bone are differentiated by means of video technology followed by computerized processing of images taken of the halves of the slaughtered animal body. The method described in DE 199 52 628 B4 presents yet another step. The method disclosed in this publication makes it possible to conduct a determination of the weights, as well as the weight and meat proportions of the various pieces, such as ham, roast, filet, shoulder, and/or belly, on the uncut halves of a slaughtered pig. Here, the method proceeds from a differentiation of image points according to whether they represent meat, fat or bone, which is comparable to the publication cited above, but also makes possible a determination of the parameters that determine the commercial value of the parts, with the help of landmarks on the contour of the halves of the slaughtered animal body and by evaluating the image points and interpolating the course and position of the backbone and the subcutaneous layer of lard. Even when the data obtained, as emphasized, make possible certain conclusions relative to cutting up the slaughtered animal body that is favorable from qualitative and economic viewpoints, the data are only useful in a limited way, in particular if they are to be used for an automated cutting up. In practice, therefore, the cutting up is carried out with the use of machines, which, however, are usually still manually guided. In the ideal case, the butcher attempts to at least utilize the knowledge obtained in the evaluation, for example, in order to cut off a filet piece in such a way that it is to the greatest extent devoid of fat or to cut up the carcass according to the results of the evaluation for the tissue calculated as the ham actually as a whole ham of corresponding quality. However, if the butcher, despite the information that is available to him relative to the properties of the meat, is instructed to a great extent by his own experience, he will finally cut up the meat for the most part based on his own subjective estimation, and thus more or less precisely. Therefore, for example, a high-priced filet piece might not be cut out to the greatest extent possible from the slaughtered animal body, or parts are separated with it which do not basically satisfy the requirements established for a filet piece, so that it must be post-processed later on, and if it is not, the qualitative expectations of the customer will not be met.

The described disadvantages are primarily caused by the fact that the above-described methods are all based essentially on a two-dimensional approach. The reason for this is again the two-dimensional nature of the images or video films serving as a basis for the calculations. By means of the so-called light-sectioning procedure, the projection of several parallel, equidistant light strips projected onto the slaughtered animal body, it is also possible to obtain volumetric information to a limited extent, but with this technique very little information is obtained which makes possible a true fully automatic cutting up with full consideration of the three-dimensional form of the respective slaughtered animal body.

With respect to establishing cutting-up points, a method is known from DE 4,109,345 C2, in which a fixed point for cutting that lies on the sacrum of the backbone is determined by means of image processing, for cutting up the halves of the slaughtered pig. Thus, the method supplies starting points for the first steps of coarse cutting up, but does not make possible an automated, detailed cutting up, which considers information on the weights of the independently treatable parts of the slaughtered animal body in a suitable manner and does not even make possible a selective separation of these parts from the points of view of quality and cost.

In particular, the method described in DE 199 52 628 B4 already provides good and accurate results on the meat quality, but possibilities for even more accurate evaluation are desired for this purpose, under continually increasing cost pressure. This desire refers both to the meat evaluation itself as well as the reciprocal relationship between the evaluation results and the cutting up of the slaughtered animal body. Thus, for example, the method described in this step assumes that the slaughtered animal body has already been cut in half. However, for example, this halving may be accompanied by errors made during the cutting in half, so-called cleavage errors, which are transmitted to the determination of the weight proportions of individual parts of the slaughtered animal body. From this aspect and in respect thereto, in order to compute the determined weight and meat proportions in a precise further cutting up of the slaughtered animal body corresponding to the results, an extensive automation and precision is also extremely desirable for this procedure.

The object of the invention is thus to provide a method which makes possible a further precision of the evaluation of slaughtered animal bodies, in particular also with respect to cutting them up automatically. Therefore, particularly by including volumetric parameters, the method will provide a more precise determination of the points for cutting up and an even more exact calculation of meat and weight proportions.

The object is solved by a method with the features of the principal claim. Advantageous embodiments or enhancements of the method according to the invention are given by the subclaims.

As has already been presented, the proposed method serves for determining physiological parameters of a slaughtered animal body with the objective of its evaluation relative to different useful purposes specific to the application. Thus the evaluation is made from a qualitative aspect for determining the commercial value for the entire slaughtered animal body or its independently processable parts or it is made in order to derive parameters for a largely automated cutting up of the slaughtered animal body. In the ideal case, which can largely be achieved by the method, the two evaluation objectives named above can finally be related to one another so that the cutting up is performed taking into consideration the evaluation results obtained relating to commercial value. For example, this means that in the course of the evaluation of a slaughtered pig, information will be obtained on the ham weight obtainable from the point of view of commercial value, which is converted into cutting parameters for cutting the pig up in such a way that the separation of the ham actually produces a piece of ham which corresponds to the ham that was predicted in terms of its weight and quality, while with the method previously practiced, the separation of such a piece that is precise in terms of volume and weight while simultaneously preserving the standards specified by the commercial classes is only theoretically attainable.

According to the method, as it is known basically, first the object, i.e., the slaughtered animal body or one of its pieces is acquired by means of an image acquisition device. Then a software-supported evaluation of the image acquired from the respective object is made. The object to be evaluated is thus acquired, however, not with a video system of the conventional, type but rather a tomographic method, such as computer tomography or nuclear spin tomography is used as the imaging method according to the invention. The application of positron emission tomography (PET) would certainly also be basically conceivable, but in preliminary experiments, computer tomography (CT) has proven to be particularly well suitable.

A disk-shaped segment or slice of the object is acquired by means of a corresponding tomograph. The obtained image is input into image-processing software, by means of which a light-and-dark and/or color-based threshold-value evaluation of the image points is conducted with respect to differentiating them as to whether they belong to the background or the object, as well as to the tissue compartments of meat, fat and bone that make up the object of the slaughtered animal body. Finally, based on what is obtained in the image processing for the assignment of image points to the object and to the compartments, a model is created that directly reproduces the contour lines as well as the arrangement and structure of the tissue compartments. The invention thus introduces tomography, which has previously been employed in the field of medical diagnostics to a completely new field of application, which has not been previously considered. It will be pointed out here that in the context of the invention, a (largely) automated cutting up is not to be conclusively made equal to a fully automated dismemberment. Certainly, this is a long-range objective that can absolutely be obtained by means of the invention, but the invention will comply with the objective that has already been established if individual complex processing steps, such as, for example, the mentioned separation of the ham or the removal of a roast of pork can be completely automated for the pig.

In the sense of the invention, of course, possibilities given by tomography can be utilized in such a way that several slices of the object—thus of a slaughtered animal body or of a part thereof—are acquired one after the other and a 3D model of the slaughtered animal body or of the parts thereof is made by joining together the acquired and processed image sequences, and this model directly reproduces the spatial arrangement and extent of the tissue compartments, thus the meat or fat regions and the bone, for the object considered each time.

When the method according to the invention is used in a way that is practically relevant, the considered or evaluated object is cycled by moving it through the tomographic imaging device, whereby the surface vector of a large principal surface of the slices or volume elements of the object acquired each time and evaluated by means of the image-processing software coincides with the direction of transport. By synchronizing the transport cycle and the image processing, the position of each image point within the 3D space can be clearly determined.

The procedure which has just been described makes it possible to incorporate the tomographic imaging device directly in a butchering and processing line or in a processing branch of such a line. Independently of the direct inclusion of the tomograph, the volume of a piece of the slaughtered animal body can be calculated by summing up or integrating several volume segments acquired by means of the tomographic method and input into the image-processing software, and finally, by summing up the percent proportions of the tissue compartments determined in the course of image processing, their multiplication by the densities of the compartments, which are known in and of themselves, and the division by the number of volume segments forming the respective piece, the mean densities of the compartments are determined. In turn, from the mean densities, the mass of the piece can be determined by multiplying by the volume. The considered piece can be established each time for a slaughtered animal body which is at least partially uncut if it belongs to a group of independently processable pieces. In this way, the boundaries of the piece within the volume of the slaughtered animal body, insofar as it is still uncut, are established by determining anatomic landmarks such as points, lines, areas and volumes in the tissue analysis of the slices.

The method according to the invention offers the possibility of determining the position and extent of the bone within the respectively considered slices, in the course of differentiating the compartments during the image processing. By means of the automatic analysis of bones or bone ends in 3D space, fixed points can thus be obtained, which form cutting parameters for a largely automated rough cutting up of the respectively considered object. This will be discussed in more detail in the explanations relative to the example of embodiment. One embodiment of the invention that is provided concerns an evaluation of the slaughtered animal body relating to its "deboning"—which is understood by the person skilled in the art also as removal of the bone or the English "deboning", which will also be discussed in more detail in connection with the example of embodiment. A rough cutting up of the entire slaughtered animal body is also conceivable proceeding from known anatomical features or reference parameters optionally filed in the system for this purpose.

The method according to the invention further makes it possible to obtain fixed points in 3D space by analysis of the volume segments relative to whether they belong to the object and to the tissue compartment of fat, which points can be used as cutting parameters for removing the fat from the object, preferably from a specific part of the slaughtered animal body. With respect to the application of the method for determining physiological parameters in the case of slaughtered pigs, a special embodiment of the method is directed to determining the thickness and the course of the subcutaneous layer of lard extending along the contour line of the back. The transition between the subcutaneous layer of lard and the tissue that bounds it is thus determined by evaluating the gradients of the brightness change in the transition from one image point to the next within one volume segment and from segment to segment or by means of a so-called nearest neighbor classification. In the first case, for the analysis proceeding forward in a specific direction on the image object, a maximum gradient, i.e., the steepest increase in brightness change indicates a transition between two tissue types, while the transition by means of the nearest neighbor classification is found by the fact that image points that are adjacent to one another opposite different starting values or reference values learned for the three tissue compartments of fat, meat, and bone, have the smallest difference in gray values. This means that one image point has, for example, the smallest difference in gray-value relative to the starting value or reference value characterizing the tissue type meat, while the adjacent image point optionally has the smallest difference in gray value relative to the starting value characterizing fat. The starting values or reference values are thus learned by the system, based on empirically obtained values.

In the course of a two-dimensional or three-dimensional evaluation, a transition line or area characterizing the transition between the tissue compartments is obtained in the manner described. The data obtained on the thickness and the course of the subcutaneous layer of lard are utilized in an enhancement of the previously explained embodiment of the method for deriving cutting parameters, which make possible a removal of fat from the rack or roast of meat by complete separation of the subcutaneous layer of fat or serve for the purpose of trimming to a certain extent the fat remaining on the back on the animal roast.

According to a particularly advantageous configuration of the method, the parameters derived relative to a rough cutting up of the slaughtered animal body or those, in the above-named case, for the removal of fat from a rack or roast are utilized directly for controlling a cutting tool. Therefore, they are transferred, for example, as position coordinates, which are utilized by step motors or linear motors for positioning the cutters.

Figure 2:
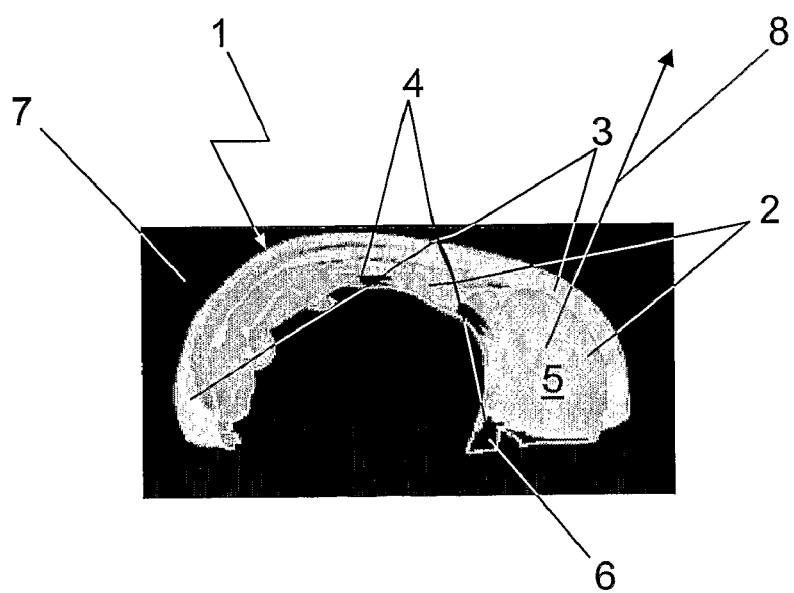

The possibilities of the method according to the invention based on FIGS. 1 and 2 will be explained once more in further detail below. Herein is shown:

FIG. 1: A volume segment or slice of the part of a slaughtered animal body comprising the rack or roast of meat which has been acquired by means of computer tomography FIG. 2: The volume segment or slice according to FIG. 1 according to the evaluation or image processing, respectively.

FIG. 1 shows, as an object 1 that stands out against a background 7, a sectional image of part of a slaughtered animal body which has been acquired by means of x-ray computer tomography (CT). This sectional image reproduced in the figure in two-dimensional representation represents a volume segment or slice of the part of a slaughtered animal body evaluated according to the method of the invention, namely a slice of the object considered with a finite thickness. This involves a slice of the so-called middle piece, which comprises a part of the belly on the left, a part of the costal arch in the center, and a part of the rack or roast on the right. FIG. 1 reproduces the raw image obtained directly from the computer tomography. This figure is now subjected to a threshold value evaluation. In this way, the individual tissue regions or compartments, respectively, are sharply bounded relative to one another, so that the image according to FIG. 2 results. The compartments can be clearly recognized in this representation. The bright regions involve fat tissue 3, while the bounding, dark-gray regions represent the meat 2. The bone 4 can be recognized in the form of the black regions in the figure. The proportions of meat, fat and bone can be clearly determined for the volume segment based on the sharp demarcation. By means of the alignment of several such parallel sectional imges, a three-dimensional model of the object 1 acquired by slices by means of CT is produced in the computer—one obtains practically a "crystal-clear slaughtered animal body" in which the position and course of individual relevant regions, such as vertebral column, belly, shoulder, ham or rack or roast 5, are no longer interpolated as they were previously on the basis of individual measurement data by mathematical calculations, such as polygonal calculations, but rather are completely and directly measured. In this way, the thickness selected for the slices acquired by means of the tomograph determines the accuracy of the measured values. Volume segments or slices, within which a specific tissue compartment is assigned to each volume part can be calculated from the slice thickness or the distances between slices, respectively, specified for the image acquisition on the tomograph. Finally, the total volume of the respective compartments of meat 2, fat 3 and bone 4 can be determined from the sum of all volume segments or slices over the entire object of the slaughtered animal body or piece thereof. In this way, the regions of large pieces can be demarcated automatically in the evaluation of slaughtered animal bodies or their halves, so that the volume and quantity data as well as the proportions of the large pieces can also be calculated prior to cutting up. Therefore, a complete evaluation of the slaughtered animal body and pieces thereof will be provided for the first time by means of a direct measurement method by means of automatic CT image evaluation.

The 3D information obtained for object 1 is utilized in the enhancement of the method for the automatic cutting up of slaughtered animal bodies and pieces thereof, wherein, with respect to the information obtained for the bone structure, specific bones or bone ends, respectively, are analyzed automatically in 3D space.

With a glance at the given example of embodiment, three-dimensional cutting paths can be established for separating the rack or roast 5 which are derived from the information for bone structure, and cutting paths for the removal of its fat can be derived from the additionally obtained information for the structure of the fat regions 3. The corresponding cutting parameters can be transferred to a cutting device, which first separates the rack or roast 5 and then this device automatically either completely removes the fat or trims the subcutaneous fat layer 3 to a specific extent that remains on rack or roast 5. A comparable procedure is also possible for other parts of the slaughtered animal body or for the slaughtered body of other butchered animals, respectively.

Another application is deboning or so-called automatic deboning. For automated cutting up, removal of fat or deboning, the piece shown in FIG. 2 as a section is transferred to a processing line, which has as a component an evaluating device operating according to the method. In this way the piece or object 1 is positioned in a defined position and alignment at or on a corresponding conveyor device, for example, a conveyor belt and fixed on the conveyor system, for example, by means of clamping, prior to the measurement process. Object 1 is cycled through the tomograph, which is not shown, by moving it along a transport direction symbolized by the surface vector 8 projecting out actually perpendicularly from the represented plane. Directly after the measurement process, with knowledge of the complete 3D information in a defined position, the cutting up, removal of fat and/or deboning is conducted, wherein the latter indicates, with a glance at FIG. 2, that the bone region 6, i.e., the backbone, which is seen to be black in the lower right corner, is separated along an established cutting path.

The image sequences of the slaughtered animal body or parts thereof, respectively, are automatically analyzed as follows for all applications (cutting up, removal of fat or deboning):
1. Acquisition of object 1 in the form of image slices or slice-form segments.
2. Determination of the outer contour by simple threshold-value limits relative to the surroundings.
3. Determination of the tissue compartments of meat 2, fat 3 and bone 4.
    3.1 Nearest neighbor classification from the previously learned starting values for meat 2, fat 3 and bone 4.
    3.2 An assignment of all image points within the outer contour to the three compartments of fat 3, meat 2, or bone 4 is produced corresponding to the smallest difference in gray value between the actual image point and the specified starting values.
    3.3 Volume elements are produced by using the slice thicknesses as well as the distances between slices and these are summed up correspondingly.
    3.4. A complete 3D model as well as the volume sums for fat 3, meat 2, and bone 4 result from all outer contours and segment slices.
    3.5. The quantities and proportions of fat 3, meat 2, and bone 4 also result due to the knowledge of the mean densities of fat 3, meat 2, and bone 4.
4. Now, beginning from the outer contour, the subcutaneous fat layer 3 (whiter relative to the region bounding the outer contour) can be determined from the 3D model with the segmenting that has been put together; this fat layer is found up to the first transition from fat 3 to meat 2 (gray region of average brightness).
5. From the three-dimensional thickness of the outer fat layer 3, a three-dimensional cutting profile can thus be determined, which can be utilized for the complete separation of the subcutaneous fat 3 or for the removal of fat so that a specific mass of fat remains, for example, on rack or roast 5, ham, belly or shoulder in the case of a pig.
6. The assignment to the conveyor system is made by attaching the object to the conveyor system and by the position indicator.
7. Positions for the cutting up or deboning, respectively, can be derived from the knowledge of the bone position for each slice image and thus in 3D space. For this purpose, the x-, y- and z-coordinates of the outer contours of the bone objects are determined for each slice image, so that a 3D bone model can be determined.
8. These coordinates are transferred to an automatic cutting up or deboning apparatus, respectively.

LIST OF REFERENCE NUMBERS USED

1 Object (slaughtered animal body or part thereof)
2 Meat (tissue)
3 Fat (tissue) or subcutaneous fat or lard layer, respectively
4 Bone
5 Cutlet or meat rack or roast
6 Bone region
7 Background
8 Direction vector

The invention claimed is:
1. A method for determining physiological parameters of a slaughtered animal body or its parts with the objective of a qualitative evaluation for determining commercial value, with respect to the weights as well as the weight proportions and meat proportions of the parts of the slaughtered animal body that can be processed independently or processed into meat products, and/or with the objective of deriving parameters for automated cutting up, wherein the slaughtered animal body or a part proceeding from the slaughtered animal body based on cutting up the slaughtered animal body is acquired using an image acquisition device and an image acquired from the slaughtered animal body or a part proceeding from the slaughtered animal body is evaluated in a software-supported manner, is hereby characterized in that the acquisition of the object is produced using a tomographic method, such as computer tomography or nuclear spin tomography, and images obtained for one or more slice-type segments of object are input into image-processing software, whereby a light-and-dark and/or color-based threshold-value evaluation of the image points is conducted with respect to differentiating these points for determining whether they belong to background or the object, as well as to tissue compartments of meat, fat and bone, forming the object of the slaughtered animal body, and based on an assignment of image points to object and compartments, a model of the object that directly reproduces contour lines as well as an arrangement and structure of the tissue compartments is prepared.

2. The method according to claim 1, further characterized in that a 3D model of the slaughtered animal body or of parts thereof is made by joining together the acquired and processed image sequences from several sequential slice-form segments, and this model directly reproduces a spatial arrangement and extent of the tissue compartments for each object that is considered.

3. The method according to claim 2, further characterized in that by summing up or integrating over several volume segments acquired using the tomographic method and input into image-processing software, the volume of a piece of the slaughtered animal body is calculated by summing up the percent proportions of the tissue compartments that were determined in the course of the image processing, which are multiplied by the densities of the compartments that are known in and of themselves and divided by the number of volume segments forming the respective piece, determining their mean density, as well as determining the mass of the piece from the product of volume and mean density, whereby each considered piece is established for a slaughtered animal body that is at least partially uncut by belonging to a group of independently processable pieces and the boundaries of the piece within the volume of the slaughtered animal body, insofar as it is still uncut, are established by determining anatomic landmarks such as points, lines, areas and volumes in the tissue analysis of the segments or slices.

4. The method according to claim 2, for determining physiological parameters for a slaughtered pig body, which is hereby characterized in that the thickness and the course of the subcutaneous layer of lard extending along a back contour line is determined, wherein a transition between a subcutaneous layer of lard and the tissue that bounds it is thus found by evaluating gradients of a brightness change in the transition from one image point to the next within one volume segment and from segment to segment each time as the maximum gradient of the brightness change, or is found by the fact that image points adjacent to one another have the smallest differences in gray value relative to the different starting values learned for the three tissue compartments of fat, meat and bone.

* * * * *